United States Patent [19]

Stoy

[11] Patent Number: 5,509,478
[45] Date of Patent: Apr. 23, 1996

[54] METHOD OF DETERMINING THE QUALITY OF STEAM FOR STIMULATING HYDROCARBON PRODUCTION

[75] Inventor: James R. Stoy, Missouri City, Tex.

[73] Assignee: Texaco Inc., White Plains, N.Y.

[21] Appl. No.: 436,665

[22] Filed: May 8, 1995

[51] Int. Cl.⁶ .................................................. E21B 47/00
[52] U.S. Cl. .................. 166/250.06; 166/272; 73/155
[58] Field of Search .................... 166/250.03, 250.06, 166/252.6, 265, 272, 303; 73/155

[56] References Cited

U.S. PATENT DOCUMENTS

| | | | |
|---|---|---|---|
| 4,228,855 | 10/1980 | Sustek, Jr. et al. | 166/250.03 |
| 4,409,825 | 10/1983 | Martin et al. | 73/155 |
| 4,458,520 | 7/1984 | Adame et al. | 73/38 |
| 4,547,078 | 10/1985 | Long et al. | 166/250.06 X |
| 4,576,043 | 3/1986 | Nguyen | 73/195 |
| 4,662,219 | 5/1987 | Nguyen | 73/195 |
| 4,681,466 | 7/1987 | Chien et al. | 73/195 X |
| 4,736,627 | 4/1988 | Wick, III et al. | 166/303 X |
| 4,836,032 | 6/1989 | Redus et al. | 73/861.04 |
| 4,958,684 | 9/1990 | Nguyen et al. | 166/252 |

Primary Examiner—Frank S. Tsay
Attorney, Agent, or Firm—Kenneth R. Priem; James L. Bailey; Richard A. Morgan

[57] ABSTRACT

A method has been discovered for determining the quality of steam reading a subterranean formation through a well bore. The steam is passed through a choke which imparts critical flow characteristics. A turbine meter is calibrated at the surface at known conditions and then positioned in the well where the steam quality value is required. The turbine meter is used in combination with the Saturated Steam Table to determine steam quality.

4 Claims, 1 Drawing Sheet

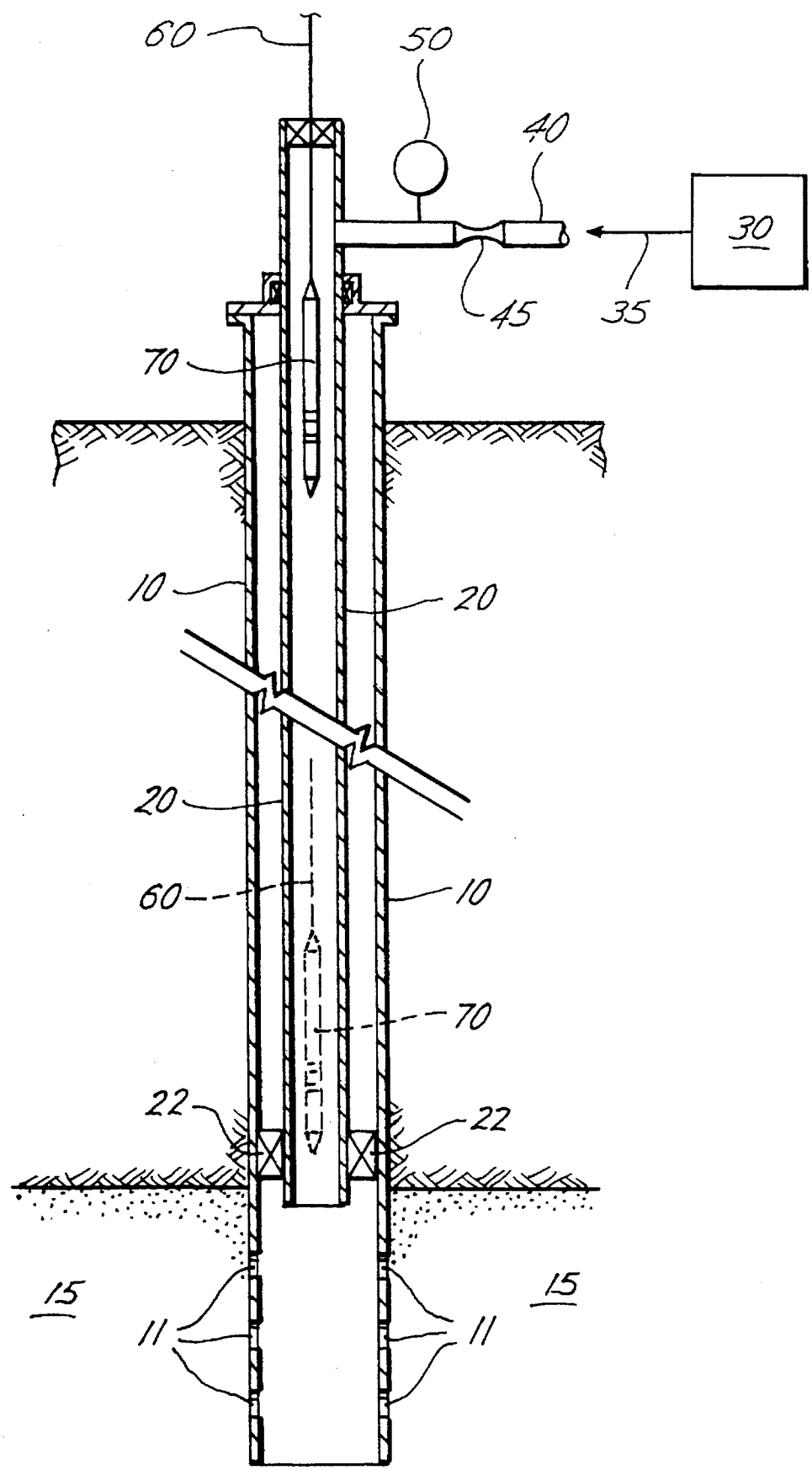

1

METHOD OF DETERMINING THE QUALITY OF STEAM FOR STIMULATING HYDROCARBON PRODUCTION

BACKGROUND OF THE INVENTION

1. Field of the Invention

This invention relates to a method of determining the quality of wet steam used for enhancing petroleum recovery from a subterranean formation.

2. Description of the Related Art

Steam flooding has become an accepted practice in oil or petroleum recovery from reservoirs that require stimulation to produce a satisfactory flow of crude petroleum. There is a need for a simple method to measure the quality of steam reaching the formation through an injection well. Such a measurement would be particularly useful in determining the amount of heat reaching the underground formation and the cost effectiveness of this type of stimulation.

The measurement of steam quality is of importance since steam quality directly affects production. The quality of the steam which can be most economically injected into a particular reservoir is dependent on a number of parameters. These include the age and hydraulic configuration of the reservoir. It is desirable that the quality of steam injected be adjusted to that quality which best stimulates the well.

The flow rate and quality of injected steam is usually monitored at the choke in the steam injection line. Steam leaves the steam generator at a measured quality pressure and mass flow rate. As the pressurized steam flow progresses toward an injection well, the quality decreases. The decrease is caused by factors as the distance the steam travels, the amount of pipe insulation, and the number and orientation of fittings.

U.S. Pat. No. 4,836,032 to C. L. Redus et al. discloses a method of determining the quality of steam for stimulating hydrocarbon production. The method relies on an orifice plate in series with a critical flow choke.

U.S. Pat. No. 4,681,466 to S. Chien et al. discloses a method of determining the quality of steam. The method makes use of pressure and temperature measurements adjacent two flow restriction means.

BRIEF DESCRIPTION OF THE DRAWING

In the Drawing is a schematic representation of a subterranean well bore with a conduit for the passage of steam and means for taking the measurements for carrying out the method of the invention.

BRIEF DESCRIPTION OF THE INVENTION

The invention is a method of determining the quality of pressurized steam flowing through a conduit to a subterranean formation. The conduit includes an upstream end in fluid communication with a steam source, optionally a choke having a constricted passage of sufficient size to give the pressurized steam critical flow characteristics, and a downstream end in direct fluid communication with a subterranean formation.

At the upstream end, the steam mass flow rate (M) is measured, preferably by means of the choke. Steam pressure ($P_s$) and steam temperature ($T_s$) are measured. From these measurements steam quality ($X_s$) is determined.

A turbine meter is positioned immediately downstream of the choke. The turbine angular velocity ($\omega_1$), indicating volumetric flow rate is measured. Pressure ($P_1$) and/or temperature ($T_1$) are measured.

The turbine meter is positioned at the conduit end. The turbine angular velocity ($\omega_2$), indicating volumetric flow rate is measured. Pressure ($P_2$) and/or temperature ($T_2$) are measured.

Steam quality ($X_2$) at the conduit downstream end is determined as a function of $X_s$ and the measurements of $P_1$, $P_2$, $\omega_1$, $\omega_2$, and M.

As a result, recovery of petroleum from the subterranean formation can be economically optimized. For example, steam mass flow rate (M) can be increased, decreased or terminated. For another example, steam quality ($X_s$) can be varied to control steam quality ($X_2$) to the subterranean formation.

DETAILED DESCRIPTION OF THE INVENTION

Reference is made to the Drawing. A well casing 10 has a tube 20 contained therein. Perforations 11 at the lower portion of well casing 10 provide direct fluid communication between tube 20 and subterranean formation 15. Packer 22 maintains the spacing between well casing 10 and tube 20 and prevents reverse flow at steam upward in casing 10. Pressurized steam 35 is supplied from steam generator 30 to steam pipe 40. Means for measuring steam mass flow rate is shown in the drawing as choke 45. Other means for measuring steam mass flow rate are disclosed in U.S. Pat. No. 5,031,465 to C. L. Redus disclosing a method using a choke and orifice plate; and U.S. Pat. No. 5,141,055 to S. Chien et al. disclosing a method using a critical flow venturi, both patents incorporated herein by reference.

Choke 45 is flanged to steam pipe 40. Choke 45 causes the steam to flow with critical flow characteristics, such as sonic velocity The mass flow rate of steam (M), steam pressure ($P_s$) and steam temperature ($T_s$) are measured by instruments designed for this purpose, graphically represented by measuring instrument 50, which is representative of flow meters such as orifice meter or turbine meter and the like and calibrated thermocouple, mercury thermometer, alcohol thermometer and pressure gauge. At critical flow the steam is saturated and the quality ($X_s$) is determined from the Saturated Steam Tables or a Mollier Diagram.

Wire 60 is attached to sonde 70. Sonde 70 contains a turbine flow meter. A turbine flow meter has a rotating member whose angular velocity ($\omega$) is measured as an indication of volumetric flow rate. Sonde 70 also includes instrumentation for measuring pressure or temperature or both temperature and pressure.

In an upper position, sonde 70 is positioned in an upper portion of tube 20, immediately downstream of choke 45. In this upper position, turbine meter angular velocity ($\omega_1$) is measured as well as pressure ($P_1$) or temperature ($T_1$) or both pressure ($P_1$) and temperature ($T_1$).

In the upper position the turbine flow meter is calibrated using mass flow rate of steam (M), and quality ($X_s$).

The sonde 70 is repositioned by means of wire 60 to a second, lower position at the tube 20 downstream end adjacent packer 22. At this lower position turbine meter angular velocity ($\omega_2$) is measured as well as pressure ($P_2$) or temperature ($T_2$) or both pressure ($P_2$) and temperature ($T_2$).

At the lower position, the volumetric flow rate is calculated from the turbine flow meter calibration. Steam quality is then calculated from the Saturated Steam Table or a Mollier Diagram.

This invention is shown by way of Example.

EXAMPLE

Reference is made to the drawing.

Steam mass flow rate (M), temperature ($T_s$) and pressure ($P_s$) are measured at instrument 50.

M=5000 lb/hr.

X=73% (Saturated Steam Table)

Sonde 70 is positioned at the upper position and the following measurements made $\omega_1$=120 rpm $P_1$=250.0 psig vg @ 250 psig=1.744 ft.$^3$/lb.

Total vapor volume calculation (upper position)

(5000 lb/hr) (73%) (1.744 ft.$^3$/lb)=6366 ft.$^3$/hr Spinner constant=6366 ft.$^3$/hr./120 rpm=53.047 ft.$^3$/rpm Sonde 70 is repositioned at the lower position.

$\omega_2$=108 rpm $P_2$=230.4 psig vg @ 230.4 psig=1.880 ft.$^3$/rpm

Vapor volume at lower position=(108 rpm) (53.047 ft.$^3$/hr/rpm)=5729 ft.$^3$/hr.

Vapor mass rate=5729 ft.$^3$/hr/1.880 ft.$^3$/lb=3047 lb/hr.

Steam Quality $X_2$=3047 lb/hr/5000 lb/hr=0.609

While particular embodiments of the invention have been described, it will be understood, of course, that the invention is not limited thereto since many modifications may be made, and it is, therefore, contemplated to cover by the appended claims any such modifications as fall within the true spirit and scope of the invention.

What is claimed is:

1. A method of determining quality of pressurized steam flowing through a conduit, which conduit includes an upstream end and a downstream end in direct fluid communication with a subterranean formation, which method includes the steps of:

(a) at the upstream end, measuring a steam mass flow rate (M), measuring a steam pressure ($P_s$) and a steam temperature ($T_s$) and determining a steam quality ($X_s$) therefrom;

(b) positioning a turbine meter proximate the upstream end, measuring an angular velocity ($\omega_1$) indication of volume flow rate, and measuring a steam pressure ($P_1$);

(c) positioning the turbine meter at the downstream end, measuring an angular velocity ($\omega_2$) indication of volume flow rate, and measuring a steam pressure ($P_2$);

(d) determining steam quality ($X_2$) at the downstream end as a function of ($X_s$) and the measurements $P_1$, $P_2$, $\omega_1$, $\omega_2$, and M.

2. A method of determining quality of pressurized steam flowing through a conduit, which conduit includes an upstream end, a choke having a constricted passage of sufficient size to give the pressurized steam critical flow characteristics, and a downstream end in direct fluid communication with a subterranean formation, which method includes the steps of:

(a) at the upstream end, measuring a steam mass flow rate (M), measuring a steam pressure ($P_s$) and a steam temperature ($T_s$) and determining a steam quality ($X_s$) therefrom;

(b) positioning a turbine meter proximate the upstream end, measuring an angular velocity ($\omega_1$) indication of volume flow rate, and measuring a steam temperature ($T_1$);

(c) positioning the turbine meter at the downstream end, measuring an angular velocity ($\omega_2$) indication of volume flow rate, and measuring a steam temperature ($T_2$);

(d) determining steam quality ($X_2$) at the downstream end as a function of ($X_s$) and the measurements $T_1$, $T_2$, $\omega_1$, $\omega_2$, and M.

3. A method of determining quality of pressurized steam flowing through a conduit, which conduit includes an upstream end, a choke having a constricted passage of sufficient size to give the pressurized steam critical flow characteristics, and a downstream end in direct fluid communication with a subterranean formation, which method includes the steps of:

(a) at the choke, measuring a steam mass flow rate (M), measuring a steam Pressure ($P_s$) and a steam temperature ($T_s$) and determining a steam quality ($X_s$) therefrom;

(b) positioning a turbine meter downstream of the choke, measuring an angular velocity ($\omega_1$) indication of volume flow rate, and measuring a steam pressure ($P_1$);

(c) positioning the turbine meter at the downstream end, measuring an angular velocity ($\omega_2$) indication of volume flow rate, and measuring a steam pressure ($P_2$);

(d) determining steam quality ($X_2$) at the conduit downstream end as a function of ($X_s$) and the measurements of $P_1$, $P_2$, $\omega_1$, $\omega_2$, and M.

4. A method of determining quality of pressurized steam flowing through a conduit, which conduit includes an upstream end, a choke having a constricted passage of sufficient size to give the pressurized steam critical flow characteristics, and a downstream end in direct fluid communication with a subterranean formation, which method includes the steps of:

(a) at the choke, measuring a steam mass flow rate (M), measuring a team pressure ($P_s$) and a steam temperature ($T_s$) and determining a steam quality ($X_s$) therefrom;

(b) positioning a turbine meter downstream of the choke, measuring an angular velocity ($\omega_1$) indication of volume flow rate, and measuring a steam temperature ($T_1$);

(c) positioning the turbine meter at the downstream end, measuring an angular velocity ($\omega_2$) indication of volume flow rate, and measuring a steam temperature ($T_2$);

(d) determining steam quality ($X_s$) at the downstream end as a function of ($X_s$) and the measurements $T_1$, $T_2$, $\omega_1$, $\omega_2$, and M.

* * * * *